United States Patent [19]
Carim

[11] 4,377,170
[45] Mar. 22, 1983

[54] NON-POLARIZABLE BIOELECTRODE
[75] Inventor: Hatim M. Carim, Saint Paul, Minn.
[73] Assignee: Minnesota Mining and Manufacturing Company, St. Paul, Minn.
[21] Appl. No.: 211,565
[22] Filed: Dec. 1, 1980
[51] Int. Cl.³ .............................................. A61B 5/04
[52] U.S. Cl. ................................... 128/639; 252/521
[58] Field of Search .............................. 128/639–641, 128/644, 783, 798, 802, 803; 252/521

[56] References Cited
U.S. PATENT DOCUMENTS

| | | | |
|---|---|---|---|
| 3,027,333 | 3/1962 | Friedman | 128/639 X |
| 3,567,657 | 3/1971 | Lichensten | 128/639 X |
| 4,114,263 | 9/1978 | Szpur | 29/630 R |
| 4,215,696 | 8/1980 | Bremer et al. | 128/641 |

FOREIGN PATENT DOCUMENTS

| | | |
|---|---|---|
| 1350368 | 4/1974 | United Kingdom . |
| 510246 | 6/1976 | U.S.S.R. ............................. 128/803 |

OTHER PUBLICATIONS
Research Disclosure No. 16113, Sep. 1977.
Research Disclosure No. 19023, Feb. 1980.
Research Disclosure No. 18729, Nov. 1979.

Primary Examiner—Lee S. Cohen
Attorney, Agent, or Firm—Cruzan Alexander; Donald M. Sell; Carolyn A. Bates

[57] ABSTRACT

A non-polarizable electrode is disclosed comprising a metallic sensing element in contact with an electrolyte gel or other conformable, electrically conductive skin-interfacing material containing dissolved electrolyte salt and an oxidizing agent. The oxidizing agent reduces the metal on the surface of the sensing element to a metal cation which reacts with the anion of the electrolyte salt to produce an insoluble compound which is deposited on the sensing element to render it non-polarizable. The preferred embodiment of the invention relates to silver/silver chloride electrodes.

17 Claims, 1 Drawing Figure

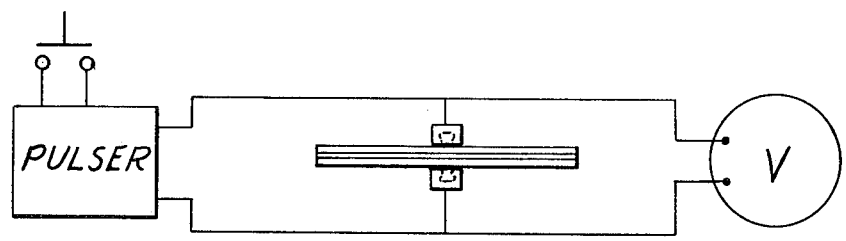

NON-POLARIZABLE BIOELECTRODE

FIELD OF THE INVENTION

This invention relates to the field of disposable biomedical electrodes, particularly disposable biomedical electrodes for picking up electrical signals from the body, such as those used to obtain an electrocardiogram.

BACKGROUND ART

A large number of disposable biomedical electrodes for heartbeat monitoring and the like are currently available. Such electrodes are designed to detect variations in the electrical potentials which appear on the skin of a patient and which reflect heartbeat activity or other electrophysiological activity. Since these skin potentials are very small—on the order of 2 millivolts—the potentials must be amplified to a considerable extent by the testing apparatus to provide effective outputs reflecting the electrophysiological activity. For this reason, electrodes must have very high performance to minimize noise factors and maximize the quality of the signals transmitted to the testing apparatus by the electrodes.

Conventional disposable ECG electrodes generally comprise an electrically conductive sensing element, preferably metal, having a substantially flat base portion or flange and a vertically-projecting pin or knob on the upper surface of the flange. The pin is either connected directly via a lead wire to the testing apparatus (one-piece connector), or it is inserted into a hollow snap connector which is, in turn, connected to the lead wire. This "male/female" snap connector arrangement is often preferred because it provides means for mechanically securing a flexible adhesive-coated material between the upper surface of the flange and base of the snap connector. The adhesive-coated material secures the electrode to the skin. A conformable, electrically-conductive interfacing material is typically used between the lower surface of the flange-portion of the sensing element and the skin to enhance electrical conductivity. The skin-interfacing material most frequently used is an electrolyte gel containing dissolved ions. Many disposable electrodes are pre-gelled during manufacture, generally by attaching a porous sponge saturated with the gel to the lower surface of the sensing element.

The majority of conventional disposable ECG electrodes are termed "silver/silver chloride" electrodes. These electrodes contain a silver or silver-coated sensing element having a layer of silver chloride deposited on the surface of the silver. It is well known that these electrodes are highly "reversible" electrochemically. When used with an electrolyte gel containing dissolved chloride ions, the electrode is able to recover rapidly after a high voltage overload, such as occurs when a patient is defibrillated. Defibrillation overload recovery is important so that the physician can obtain immediate feedback on the state of the patient's heart.

The formation of silver chloride on the silver sensing element has become as much an art as a science as can be gathered from the published literature such as the classical work of Ives and Janz in "Reference Electrodes", 1961, Academic Press, pages 179 to 226.

Electrochemically depositing a layer of silver chloride on the silver sensing element is perhaps the most common method employed. One major disadvantage of this method is that the entire surface of the silver substrate is coated with silver chloride, even though only the lower surface of the flange (which is the only part of the sensing element in contact with the electrolyte gel) requires chloriding. The result is that, in an electrode having a one-piece connector, the lead wire from the test apparatus contacts a silver chloride element. This may result in inferior electrical contact because the electrical resistivity of silver chloride is much greater than that of metal, particularly silver. A further complication associated with chloriding the entire surface of the sensing elements is that, in electrodes having a two-piece snap connector, the metal snap connector reacts chemically with the silver chloride on the sensing element to which it is anchored and undergoes oxidation. This is a common and serious problem associated with silver/silver chloride electrodes. Such reactions between the silver chloride on the sensing element and the metal snap will induce spurious signals, i.e., electrical noise or artifact in the normal ECG. To solve this problem, many electrode manufacturers have chosen to silver plate the metal snap connector. This greatly increases the cost of the electrode, and is therefore not a desirable solution.

Several alternatives have been suggested to avoid the need to deposit silver chloride electrochemically over the entire surface of the sensing element. British Pat. No. 1,350,368 describes a sensing element made by roll-bonding a thin layer of silver chloride material to a silver substrate. The manufacturing process undoubtedly involves the use of special machines and is a multi-step procedure which is a disadvantage, particularly inasmuch as the silver chloride and the silver are in a fragile form during assembly.

U.S. Pat. No. 4,114,263 describes a method wherein the portion of the sensing element that is exposed to the electrolyte gel can be selectively chlorided by the passage of a D.C. electrical charge. This method is not desirable from a manufacturing standpoint since it requires that a high quantity of electrical charge be passed in a very short time interval. Furthermore, a high chloride-containing electrolyte in contact with the silver sensing element is necessary.

An additional problem often encountered with pre-gelled disposable silver/silver chloride electrodes is the gradual decomposition of silver chloride to metallic silver and chloride ions. Decomposition may result from a number of factors including leakage of the electrolyte gel from the gel chamber to the metal snap connector, and chemical impurities in the silver chloride and/or the gel. Such factors cause local galvanic cells to form which reduce silver chloride to silver metal. As the silver chloride decomposes, the electrode loses its ability to recover after defibrillation overload.

Accordingly, prior to the present invention, the need existed for a low-cost disposable ECG electrode having the ability to recover after defibrillation overload. In particular, the need existed for a disposable silver/silver chloride electrode in which the silver chloride was deposited only on the portion of the sensing element in contact with the electrolyte gel and decomposition of the silver chloride with age was eliminated.

The present invention effectively fulfills the aforementioned need by providing an electrode in which silver chloride (or like material necessary to provide recovery after defibrillation overload) is deposited on the portion of the sensing element contacting the electrically-conductive interface material, e.g., gel, continuously during the life of the electrode. This is accomplished chemically by incorporating the necessary chemical agents into the skin-interfacing material.

It is known that an electrode comprising a solid silver sensing element in contact with an electrolyte gel of high (e.g., 2.5%) chloride ion concentration will have some silver chloride formed on the sensing element. Although claimed as a silver/silver chloride electrode, the quantity of silver chloride formed on the surface of the solid silver sensing element is vanishingly small. The reaction of the sodium chloride in the gel electrolyte forms only an infinitesimal amount of silver chloride on the silver surface. This amount of silver chloride under certain circumstances of use, such as during a defibrillation procedure, is consumed by the electrical charge passed through the electrode. Hence, the electrode is polarized to undesirably high voltages which leads to long ECG trace recovery times. Furthermore, the use of the high chloride content in the gel tends to cause skin irritation.

The present invention involves the incorporation of an oxidizing agent into the electrically-conductive interface material to facilitate the deposition of silver chloride or functionally equivalent material on the sensing element. It is known that an oxidizing agent added to a solution containing chloride ions and metallic silver will result in the production of silver chloride. Such a technique has been used to form a silver halide layer on reference electrodes used for ion-selection membrane electrodes (Research Disclosure, No. 19023, February, 1980 and Research Disclosure, No. 18789, November, 1979). However, these electrodes are not subjected to the considerable quantities of electrical charge to which a conventional pregelled disposable electrode is exposed, such as during a defibrillation procedure. Prior to the present invention, oxidizing agents have not been incorporated into electrically conductive skin-interfacing materials such as electrolyte gels used in biomedical electrodes to provide continuous deposition of silver chloride or like material on the sensing element during the life of the electrode.

DISCLOSURE OF THE INVENTION

The present invention provides a disposable, non-polarizable biomedical electrode comprising an electrical impulse sensing element having a metallic surface, a lower skin-directed surface and an upper surface having means for electrical connection to an electromedical testing apparatus. A conformable electrically-conductive skin-interfacing material is placed in intimate contact with the lower skin-directed surface of the sensing element. The interfacing material comprises a solvent having dissolved therein an oxidizing agent capable of oxidizing the metal at the surface of the sensing element to form metallic cations, and an electrolyte salt in sufficient quantity to render the interfacing material electrically-conductive. The anion of the electrolyte salt must be capable of reaction with the metallic cation to form an insoluble compound at the surface of the sensing element which causes the electrode to be non-polarizable.

The term "conformable" as used herein to refer to the skin-interfacing material means that the material will conform to the surface of the skin beneath the sensing element to provide a high surface area of contact between the skin and the sensing element.

The term "non-polarizable" refers to the ability of the electrode to recover rapidly after a high voltage overload of the type encountered during defibrillation of a patient. Specifically, the term means that the absolute value of the polarization potential of a pair of electrodes connected together through their respective interfacing materials does not exceed 100 mV, 5 seconds after a 10 volt, 100 millisecond square-wave pulse, as specified in the test method described below.

The preferred embodiment of the invention relates to an electrode in which the sensing element has a surface formed of metallic silver. The skin-interfacing material is a conventional electrolyte gel containing dissolved chloride ions to which has been added an oxidizing agent capable of oxidizing silver to the silver ion. The oxidizing agent causes the formation of a layer of silver chloride on the surface of the sensing element in contact with the gel. Although the silver/silver chloride system is the preferred embodiment of the invention, other non-polarizable systems as discussed hereinafter are also included within its scope.

The electrode of the present invention effectively overcomes the deficiencies of the prior art discussed above. The number of manufacturing steps in the making of a true silver/silver chloride sensing element are reduced since the silver substrate of the sensing element need not be coated with silver chloride during the manufacture of the electrode. In this invention, the skin-interfacing material, e.g., electrolyte gel, chemically converts part of the silver of the sensing element to silver chloride, and its action starts the moment the silver and gel come into contact. Hence, all of the silver chloride is present at the gel-silver interface only, where it is required. The remainder of the sensing element is unchlorided. This eliminates the problem of corrosion between the snap connector and the sensing element frequently encountered in prior art electrodes.

When utilizing a single-piece silver-plated sensing element the external equipment connector can be attached to a silver surface (rather than a silver chloride surface as in the prior art) which provides a highly desirable, low resistance electrical connection resulting in an improved signal-to-noise ratio.

The present invention also allows an improvement in electrode constructions wherein an adhesive-coated resilient sheet is sandwiched between the metal snap and upper surface of the flange of sensing element. In prior art electrodes wherein the entire surface of the sensing element contained a layer of silver chloride, a tight seal between the adhesive and the silver chloride was difficult to achieve because of the porosity of the silver chloride layer. Electrodes made in accordance with the present invention provide for a tighter seal as the bond between silver and the adhesive on the resilient sheet material is less prone to leakage than a bond between a porous silver chloride layer and adhesive. This minimizes migration of the electrolyte gel towards the metal snap, thereby reducing the oxidation and corrosion of the snap metal.

Furthermore, in electrodes of the present invention, the quantity of silver chloride formed on the silver sensing element increases as a function of time. By altering the composition of the interfacing material, many different profiles of quantity of silver chloride formed vs. time may be achieved. This is important, because as mentioned earlier, the conversion of silver chloride to silver is an undesirable feature in prior art electrodes. Electrodes made in accordance with the present invention have a longer shelf life than conventional Ag/AgCl electrodes. They have ample silver chloride remaining after defibrillation, and do not require excessive quantities of silver chloride on the sensing element at the time of manufacture to compensate for degradation while on the shelf.

Yet another important feature of this invention relates to the fact that substances intended to be used in contact with human skin should not contain a significant number of microorganisms. Hence, a bactericidal agent is generally included in most electrolyte gels. The oxidizing agent in the skin-interfacing material of the present invention may be selected to provide disinfectant or preservative action. This permits the omission of commonly used perservatives such as the methyl and propyl parabens in prior art gels.

DETAILED DESCRIPTION

The disposable biomedical electrode of the present invention may be constructed in any conventional manner known in the art. An electrical impulse-sensing element having a metallic surface is required. The sensing element preferably has a substantially flat base portion, the lower surface of which is placed over the skin during use and the upper surface of which has means for electrical connection to a lead wire from an electromedical testing apparatus. Preferably, the upper surface of the sensing element has a pin or stem extending vertically therefrom. In a one-piece connector assembly, the lead wire is attached directly to the pin of the sensing element. Preferably, the pin is anchored to a metallic snap connector in the manner described in U.S. Pat. No. 3,805,769. The lead wire is then connected to a protuberance of the snap connector. Preferably, the sensing element is formed of silver or silver-plated plastic. Silver is preferred because, in combination with a silver halide or silver sulfide, it forms an excellent non-polarizable electrode. However, other metals capable of forming nonpolarizable electrodes according to the present invention such as lead/lead sulfate or thallium/thallium chloride may also be used.

A conformable skin-interfacing material is attached in intimate contact with the lower surface of the sensing element. The skin-interfacing material comprises a solvent in which is dissolved an oxidizing agent capable of oxidizing the metal on the surface of the sensing element. Also dissolved in the solvent is an electrolyte salt, the anion of which is capable of reacting with the oxidized metal to form an insoluble compound which deposits on the surface of the sensing element in contact with the skin-interfacing material. This compound, in combination with the metal forms a non-polarizable electrode. The anions must be in excess of those reacting with the metallic ions to the extent necessary to provide sufficient electrical conductivity to the electrode. Preferably, the solvent is an aqueous gel of the type conventionally used in pregelled disposable electrodes. A particularly preferred gel is "LECTRON III" gel sold by Pharmaceutical Innovations, Newark, New Jersey. Guar gum gels such as those described in copending application Ser. No. 72,230, filed Sept. 14, 1979, are also useful and have the added advantage of not leaving a messy residue behind on the skin. Nonaqueous solvents such as propylene glycol have also been found to be useful. Ionic pressure-sensitive adhesive/polyhydric alcohol compositions such as those described in copending application Ser. No. 114,565, filed Jan. 23, 1980, may also be used. Nonaqueous systems are desirable because they do not dry out during use and generally require less expensive packaging.

The choice of oxidizing agent and the concentration thereof in the solvent is dependent on a number of criteria including (1) the oxidizing power of the agent, (2) its biocompatibility with skin, (3) the time available for oxidation to occur, i.e., estimated time between manufacture and use, and (4) compatibility with the particular electrolyte salt of interest. For silver/silver chloride electrodes, preferred oxidizing agents include sodium chlorite ($NaClO_2$), sodium chlorate ($NaClO_3$), sodium chromate ($NaCrO_4$), potassium dichromate ($K_2Cr_2O$), sodium hypochlorite ($NaOCl$) and para-benzoquinone. Sodium chlorite satisfies all of the above criteria, and is the especially preferred oxidizing agent for use in the present invention.

The exact chemical reactions governing the formation of silver chloride as a result of the oxidation of silver by $NaClO_2$ (or any of the other oxidizing agents) are not fully understood. It is understood that the reaction conditions should allow an oxidation-reduction reaction to occur in which silver metal loses one electron to become silver cation ($Ag^+$) and a chloride anion ($Cl^-$) should be available to form insoluble silver chloride ($AgCl$).

Whether or not a particular reaction will occur spontaneously in this respect can be predicted by reference to a standard table of half-cell electromotive force (emf) values (i.e. oxidation-reduction potentials as found in: Latimer, W. M., *The Oxidation States of Elements and Their Potentials in Aqueous Solution*, 2nd edition, New York: Prentice-Hall, Inc., 1952). Any reaction will occur spontaneously if the sum of the emf values for the oxidation half-reaction and the reduction half-reaction is positive, and the components are at unit activity.

For example, the preferred oxidizing agent for use in chloriding the silver element is sodium chlorite ($NaClO_2$). When sodium chlorite is added to acid solution, it disproportionates into a reduced species, hypochlorous acid ($HOCl$), and an oxidized species, chlorine dioxide ($ClO_2$). Both of these species are capable of oxidizing silver as shown below, if one assumes electrons may be employed in the reactions as written for emf calculations.

| Half-Cell Reaction | emf (volts) |
|---|---|
| (1) oxidation $Ag \rightarrow Ag^+ + e^-$ | −0.80 |
| reduction $ClO_2 + e^- \rightarrow ClO_2^-$ | 1.16 |
| net $Ag + ClO_2 \rightarrow Ag^+ + ClO_2^-$ | 0.36 |
| (2) oxidation $Ag \rightarrow Ag^+ + e^-$ | −0.80 |
| reduction $HOCl + H^+ + e^- \rightarrow Cl^- + H_2O$ | 1.49 |
| net $Ag + HOCl + H^+ \rightarrow Ag^+ + Cl^- + H_2O$ | 0.69 |

Applying reaction (1) to $NaClO_2$, chlorine dioxide which was generated from sodium chlorite becomes reduced to reform sodium chlorite in the process of oxidizing silver metal to ionic silver. This reaction proceeds spontaneously with a net reaction potential of 0.36 volts.

Similarly, hypochlorous acid, also generated from sodium chlorite, oxidizes silver metal to ionic silver and in the process forms chloride anion ($Cl^-$) with a net reaction potential of 0.69 volts as shown in reaction 2.

The generation of chloride ion ($Cl^-$) in reaction (2) is helpful because the chloride continues to react with the silver ion ($Ag^+$) formed on the surface of the silver sensing element to produce the desired silver chloride coating.

From the emf calculations similar to those applied to reactions 1 and 2, one also calculates that hypochlorous acid is capable of oxidizing chlorine dioxide, producing, respectively, chloride ($Cl^-$) and chlorate ($ClO_3^-$). Thus, the final reaction products of an acid solution of sodium chlorite in the presence of silver metal appear to be $Ag/AgCl$, $Cl^-$, $ClO_2$ and $ClO_3^-$.

In the calculations of reaction potentials, it is understood that the values refer to the standard state of the reactants, i.e., the reactants are assumed to be at unit activity, although this is not realized in practice.

It has been observed that with a given concentration of sodium chlorite, the amount of silver chloride formed depends on the pH of the solvent in which it is contained. Silver sensing elements kept in contact with a chlorite-containing solvent at an acidic pH showed higher amounts of silver chloride formed, as compared to those kept in contact with a neutral pH. The dissociation and reactions of the chlorites are pH-dependent and an electrolyte containing chlorite at a higher pH can be shown to retain its oxidizing power.

As a general rule, the skin-interfacing material of present invention will have a pH in the range of 4 to 8 which range has been shown to be compatible with human skin. For the majority of oxidizing agents, other than sodium chlorite, a pH below 7 is generally required to obtain formation of a sufficient amount of silver chloride, particularly at low concentrations of the oxidizing agent. Sodium chlorite has been discovered to provide adequate chloriding at neutral or higher pHs.

In the electrodes containing sodium chlorite as the oxidizing agent, the preferred concentration range has been found to be 0.001% by wt. to 0.075% by wt. of the skin-interfacing material. This concentration range has been found to be more than adequate on the basis of: (a) the amount of silver chloride formed on the silver sensing element (b) the pH range of the gel; (c) skin-irritation; and (d) the presence of chloride ion in small concentrations e.g., 1.0% by weight or less. Of course this range may be extended depending on the conditions of the composition and use.

In addition to the oxidizing agent, another essential ingredient in the skin-interfacing material is an electrolyte salt. The anion of this salt is necessary to react with the oxidized silver ion (when the oxidizing agent itself does not provide the anion). Additionally, an electrolyte salt is necessary to provide adequate conductivity to the interfacing material. The preferred salts for use in silver/silver chloride electrodes are potassium chloride (KCl) and sodium chloride (NaCl). The anion of the salt should be the same as the anion of the compound formed on the sensing element, e.g., in a silver/silver bromide electrode, bromide electrolyte salts would be used.

The concentration of the electrolyte salt in the skin-interfacing material is determined by the properties desired in the electrode sensing element and biocompatibility with the skin for the intended time of application. High chloride ion concentrations, i.e., approximately 1.5% by weight and higher have been shown to be potentially skin-irritating for long-term use such as for 24 hrs. or several days. However, for short term use, concentrations as high as 5% by weight can be tolerated. The preferred concentration of chloride ion is in the range of 0.25 percent to 0.75 percent by weight of the composition. The preferred concentration of chloride ion is 0.5 percent by weight.

In the preferred embodiment of the invention, electrodes are constructed as described in U.S. Pat. No. 3,805,769, the disclosure of which is incorporated herein by reference. The sensing element is preferably a silver-plated plastic part which is anchored to a stainless steel snap connector. The skin-interfacing material is a conventional electrolyte gel such as "LECTRON III" gel containing 1 percent by weight of potassium chloride to which has been added sodium chlorite in a concentration of 0.02 percent by weight. The gel is held in contact with the silver sensing element by being impregnated in a polyurethane sponge.

An alternative embodiment is to impregnate the sponge with an aqueous solution, e.g., 10 percent by weight, of sodium chlorite. The sponge is then dried and placed over the sensing element of the electrode. The sponge is wetted by the standard "LECTRON III" gel (containing 1 percent KCl) just prior to use. This method of practicing the invention is advantageous in several respects: (a) The oxidizing agent in a dry state in the presoaked foam has a relatively indefinite shelf life; (b) Not only the oxiding agent but extra salts, e.g., KCl, may also be used in presoaking. (c) The oxidizing agent contacts the silver or other sensing element only (not dispersed in the gel) and hence is removed from immediate contact with the skin. This lowers its irritation potential and allows higher concentrations to be used.

Another method of reducing skin irritation from contact with the oxidizing agent is to layer the skin-interfacing material and provide the oxidizing agent only in the layer contacting the sensing element. Such a layering technique would be especially useful if a non-polarizable system other than silver/silver chloride is used such as lead/lead sulfate where more toxic substances may be involved.

Test Methods

The electrodes of the present invention are "non-polarizable", i.e., they recover rapidly after a high voltage overload. Specifically, the absolute value of the polarization potential of a pair of electrodes connected together (skin-interfacing material to skin-interfacing material) does not exceed 100 mV, 5 seconds after a 10 volt, 100 millisecond square wave pulse as specified in the "Polarization" test described below.

Polarization test—This test measures the electrode's ability to permit the ECG trace to return after defibrillation. The test is to be conducted as follows:
1. A pair of electrodes are connected skin-interfacing material-to-skin-interfacing material and connected to the test apparatus (FIG. 1) with the switch open.
2. After a few seconds, the offset voltage on the voltmeter in millivolts (mV) is noted at $t=0$ seconds.
3. The switch is closed long enough to produce a 10 V, 100 mSec pulse at output into the electrode pair. Simultaneously a stop watch is started.
4. At $t=5$ sec., the offset voltage on the voltmeter in V is noted. This is pulse No. 1.
5. After 15 seconds, the offset voltage is again noted as at $t=0$.
6. The switch is again closed to produce a 10 V, 100 mSec pulse and the stop watch started.
7. The offset voltage at $t=5$ sec. is noted. This is pulse No. 2.

8. Further pulses may be given according to the same procedure.

DC offset voltage test—The DC offset voltage is measured by connecting two electrodes skin-interfacing material to skin-interfacing material to form a circuit with a DC voltmeter having minimum input impedance of 10 Megohms and a resolution of 1 mV or better. The measuring instrument applies less than 10 nA of bias current to the electrodes under test. The measurement is made after a 1 minute stabilization period, but before 1.5 minutes have elapsed. In this test, a pair of electrodes should, after a 1 minute stabilization period, exhibit an offset voltage no greater than 100 mv.

AC impedance test—The impedance of a pair of electrodes connected skin-interfacing material to skin-interfacing material can be determined by applying a sinusoidal current of known amplitude and observing the amplitude of the resulting potential across the electrodes. The magnitude of the impedance is the ratio of the voltage to the amplitude of the current. An adequate current generator can be assembled utilizing a sinusoidal signal (voltage) generator with a 1 Megohm (or greater) resistor in series with the electrode pair. The level of the impressed current should not exceed 100 microamp peak to peak. In this test, the impedance of a pair of electrodes should not exceed 3 Kilohms at 10 Hz.

The invention is further illustrated by the following non-limiting examples.

EXAMPLE 1

In this example, the amount of silver chloride formed using various oxidizing agents was measured.

One hundred milliliters of each of the following test solutions were made up, each having a molarity of 1.

| No. | Oxidizing Agent | | Wt. Appx. gms | pH |
|---|---|---|---|---|
| 1. | Sodium Chloride | NaCl | 5.9 | 8.9 |
| 2. | Sodium Chlorite | $NaClO_2$ | 9.0 | 9.6 |
| 3. | Sodium Chlorate | $NaClO_3$ | 10.6 | 8.75 |
| 4. | Sodium Chromate | $Na_2CrO_4$ | 16.2 | 9.4 |
| 5. | Potassium Dichromate | $K_2Cr_2O_7$ | 29.4 saturated | 3.75 |
| 6. | Potassium Perchlorate | $KClO_4$ | 13.9 saturated | 8.45 |

In Test A, a 1 ml sample of each test solution was placed in a test tube, and three silver-plated sensing elements were immersed therein for 15 minutes. At the end of this period, the sensing elements were washed with distilled water, air-dried, and set aside for testing. In Test B, the same procedure was followed except 10 ml of 6 M HCl were added to each test tube, and 1 ml sample of each of the resulting solutions used.

Each of the sensing elements were then electrochemically deplated, i.e., the silver chloride was reduced to silver by a constant current, and by noting the time required, the equivalent electrical charge corresponding to the quantity of silver chloride on the sensing element (hereinafter referred to as coulomb equivalents) was determined. Results are shown in the following Table I.

TABLE I

| No. | Oxidizing Agent | Silver Chloride (as millicoulomb equivalents) | Oxidizing Agt | Silver Chloride (as millicoulomb equivalents) |
|---|---|---|---|---|
| 1. | NaCl | 0 | NaCl + HCl | 0 |
| 2. | $NaClO_2$ | 250 | $NaClO_2$ + HCl | 800 |
| 3. | $NaClO_3$ | 0 | $NaClO_3$ + HCl | 675 |
| 4. | $Na_2CrO_4$ | 0 | $Na_2CrO_4$ + HCl | 525 |
| 5. | $K_2Cr_2O_7$ | 0 | $K_2Cr_2O_7$ + HCl | 425 |
| 6. | $KClO_4$ | 0 | $KClO_4$ + HCl | 0 |

From Table I it is concluded that oxidizing agents 2–5 are effective in converting Ag to AgCl in the presence of $Cl^-$ ions in the solution, whereas only $NaClO_2$ is effective in the absence of HCl.

EXAMPLE 2

This example illustrates the effect of $Cl^-$ ion concentration of the formation of AgCl using $NaClO_2$ as the oxidizing agent.

The chloride ion is necessary in the skin-interfacing material of a Ag/AgCl sensing element system to prevent polarization. Table II below shows the inhibiting effect of an increase in the chloride ion concentration in the formation of AgCl on Ag by a fixed concentration of $NaClO_2$. Silver-plated plastic sensing elements were immersed in various electrolyte gels contained in glass jars and kept in an oven maintained at 100° F. to accelerate the reactions. A few of the silver elements so immersed were randomly chosen and removed periodically. The quantity of AgCl deposited on them was determined coulometrically as described in Example 1. The electrolyte gel is "LECTRON III" (Pharmaceutical Innovation Co., Newark, N.J., described in U.S. Pat. No. 3,989,050.) to which the $NaClO_2$ was added.

TABLE II

| Time reacted. (Days at 100° F.) | % [$Cl^-$] + % [$NaClO_2$] | Silver Chloride (as millicoulomb equivalents) |
|---|---|---|
| 8 | .476 + .1 | 1355, 870, 720 |
|  | 9.52 + .1 | 435, 105, 0 |
| 30 | .476 + .1 | 1500, 1230, 990, 1500 |
|  | 9.52 + .1 | 45, 0, 90, 75, 75 |
| 42 | .476 + .1 | 1905, 2010, 1490, 1950, 1410 |
|  | 9.52 + .1 | 126, 90, 3, 9, 105, 30 |

It appears that as the chloride ion increases, $NaClO_2$ must also increase for effective plating. For most disposable Ag/AgCl electrodes used for ECG's, the concentration of chloride ion in the electrolyte gel ranges from 0.5% to 5% by weight or greater. For this range the $NaClO_2$ would have to range up to 0.1% by weight. It has been found that both $Cl^-$ and $NaClO_2$ concentrations in the higher values of the range to 5% and 0.1% respectively could cause skin irritation, especially where the protocol for preparation at a site for ECG electrode application calls for skin abrasion. In electrodes of the present invention with sodium chlorite-containing skin-interfacing material, the preferred concentration range of $NaClO_2$ has been found to be 0.001% by weight to 0.075% by weight.

It has been found that sensing elements of Ag can be plated with AgCl by $NaClO_2$ or NaOCl alone in distilled water or a gel without additional $Cl^-$ ions. As indicated above, the reversibility or polarization characteristics of Ag/AgCl systems depends on the presence of excess Cl⁻ ion in the skin-interfacing material. Electrodes otherwise identical to "RED DOT" brand electrodes No. 2246 sold by 3M Company, were made with silver plated plastic sensing elements and filled with "LECTRON III" gel containing 0.025% $NaClO_2$ with no other salts. Electrodes were aged at room conditions for 10 days, and the following electrical properties determined.

TABLE III

| Electrode Pair No. | Impedance[1] at 10Hz (ohms) | Impedance[1] at 100KHz (ohms) | Polarization[2] (in mV) at t = 0 | at t = 5 sec |
|---|---|---|---|---|
| (1) | 1300 | 500 | 1.7 | 99 |
| (2) | 1000 | 460 | 2.5 | 162 |
| (3) | 750 | 280 | .8 | 51 |
| (4) | 1500 | 740 | 1.4 | 132 |

[1]Impedance was measured using a Hewlett Packard Model No. 4800A Vector Impedance Meter.
[2]t = 0: immediately before passing a 10 volt, 100 millisecond pulse
t = 5 secs: 5 seconds after passing a 10 volt, 100 millisecond pulse.

The quantity of AgCl (in millicoulomb equivalents) on the sensing elements of electrodes not subjected to the polarization test above was 75 and 90. The data show that a considerable quantity of AgCl was formed on the Ag. However, the electrodes were not sufficiently reversible (i.e., non-polarizable) as seen by the numbers in the last column under "Polarization". Clearly, the reversible Ag/AgCl reaction can take place fast enough only in the presence of Cl⁻ ions in the electrolyte gel. Further, the absence of a salt such as KCl that could have provided the necessary Cl⁻ ions shows up as a high resistance value at 100 KHz which is indicative of the resistivity of the gel alone.

The value "Impedance at 10 Hz" (TABLE III) is a measure of the impedance of the gel plus the impedance of the Ag/AgCl/gel interface. The impedance at 100 KHz primarily reflects the impedance of the gel/electrolyte alone. To determine the effect of omitting the oxidizing agent $NaClO_2$ in the electrode gel, the following experiment was conducted. "RED DOT" Brand 2256-type electrodes were made using silver-plated plastic sensing elements and "Lectron III" gel containing KCl. After several days of aging at room conditions they were tested in pairs for electrical properties, and following results were obtained.

TABLE IV

| Pair No. | Electrode gel | Days aged | Offset Potential (mV) | Impedance at 10Hz (ohms) | Polarization[1] 10V, 100 mSec (in mV after 5 sec.) |
|---|---|---|---|---|---|
| (1) | LECTRON III 2% KCl | 10 | .4 | 710 | 90 |
| (2) | LECTRON III 2% KCl | 10 | .1 | 720 | 59 |
| (3) | LECTRON III 2% KCl | 3 | 7 | 550 | 188 |
| (4) | LECTRON III 2% KCl | 3 | 1.3 | 540 | 177 |
| (5) | LECTRON III 1% KCl | 3 | 2.3 | 660 | 304 |
| (6) | LECTRON III 1% KCl | 3 | .6 | 660 | 250 |
| (7) | LECTRON III 20% KCl | 3 | 2.5 | 140 | 210 |
| (8) | LECTRON III 20% KCl | 3 | 3 | 141 | 200 |

[1]5 seconds after passing a 10 volt, 100 millisecond pulse

TABLE V

| Gel | Silver Chloride (as millicoulomb equivalents) | |
|---|---|---|
|  | After 3 days | After 10 days |
| 1% KCl | <2 | 4,5 |
| 2% KCl | <2 | — |

The data show that after the gel has been in contact with the Ag element for three days, none of the electrode pairs had a polarization value of less than 100 mV. This is supported by the fact that the quantity of AgCl found on the sensing elements as shown in Table V is insufficient. Whenever the quantity of AgCl in mC equivalents is less than the quantity of electrical charge passed due to the polarizing pulse, the electrode will show a sluggish response, i.e., a slow recovery of its original voltage as indicated by the high mV value at 5 secs.

It can be observed from Table IV that electrodes aged for 10 days show slightly better polarization (lower mV). It is known that Ag in contact with a Cl ion-containing solution such as in the electrodes of Table IV, when aged for several months could acquire a certain small quantity of AgCl by chemical reactions. This method of formation of AgCl is very slow, unpredictable and shows large variations in the electrical properties such as impedance and polarization.

EXAMPLE 3

This example relates to electrodes made using the various oxidizing agents described in example 1 and further illustrates the effect of pH on the formation of AgCl.

Five grams of $NaClO_3$ in 5 ml of warm aqueous solution was added to 95 g of "LECTRON III" gel containing approximately 1% Cl⁻ ion to give a final gel weight of 105 g having a pH of 5.9. "RED DOT" Brand 2256-type electrodes with silver-coated plastic sensing elements were filled with the final gel mixture. Concentrated hydrochloric acid (HCl) was added to a portion of the above gel mixture until a pH of 4 was achieved. Electrodes were filled with this gel. All electrodes were aged for 10 days at room conditions and then tested for electrical properties. Results are shown in Table VI below.

TABLE VI

| Electrode Pair No. | Gel | pH | Impedance at 10 Hz (ohms) | Polarization[1] t = 0 (mV) | t = 5 sec. (mV) |
|---|---|---|---|---|---|
| (1) | LECTRON III 2% KCl + 5% $NaClO_3$ | 5.9 | 750 | .4 | 64 |
| (2) | LECTRON III 2% KCl + 5% $NaClO_3$ | 5.9 | 650 | .0 | 56 |
| (3) | LECTRON III 2% KCl + 5% $NaClO_3$ | 5.9 | 630 | .6 | 141 |
| (4) | LECTRON III 2% KCl + 5% $NaClO_3$ | 4 | 390 | .8 | 21 |
| (5) | LECTRON III 2% KCl + 5% $NaClO_3$ | 4 | 270 | .2 | 17 |

[1]t = 0: immediately before passing a 10 volt, 100 millisecond pulse.
t = 5 sec: 5 seconds after passing a 10 volt, 100 milliseconds pulse.

Standard limb lead ECG recordings were made using electrode pairs (4) and (5) above (before testing impedance and polarization) and excellent tracings were obtained on a three channel "Marquette" ECG recorder (Marquette Electronics, Inc., Milwaukee, Wis.).

The data in Table VI show acceptable polarization voltage values for the electrodes containing gel at a pH of 4, whereas the polarization for the electrodes containing gel at pH 5.9 were undesirable. It was shown in Table I that the oxidizer $NaClO_3$ is effective in forming AgCl with lower pH electrolytes and hence the data in Table I are corroborated by the data in Table VI. The other oxidizing agents listed in Table I were also incorporated in the gel and made into electrodes. Very good ECG traces were obtained and the electrical characteristics were comparable to those of conventional Ag-/AgCl electrodes.

EXAMPLE 4

This example illustrates electrodes utilizing a silver/silver bromide non-polarizable system. In a 99 g sample of "LECTRON III" gel containing no salts was dissolved 1 g of reagent-grade potassium bromide (KBr). The pH of the gel changed from 6.2 to 5.9 after addition of KBr. To a second 94 g sample of the "LECTRON III" gel (with no salts) were added 1 g of KBr and 5 gms of potassium dichromate ($K_2Cr_2O_7$). The mixture was stirred in a beaker until the salts dissolved. The pH was observed to be 5.5. This was raised by mixing a few drops of KOH to a pH of 5.9. The gel viscosity appeared lower. "RED DOT" Brand No. 2246-type electrodes with Ag-plated sensing elements were filled with the above gel mixtures and tested for ECG acquisition efficacy and electrical characteristics. Very good trace quality ECG recording were obtained with both gel mixtures. Test results are shown in the following Table VII.

TABLE VII

| Electrode pair | Gel | pH | Impedance at 10Hz (Kohms) | Polarization[1] (in mV) | |
|---|---|---|---|---|---|
| | | | | t = 0 | t = 5 |
| (1) | 1% KBr | 5.9 | 1.2 | .2 | 16.4 |
| (2) | 1% KBr | " | 1.2 | 0 | 16.8 |
| (3) | 1% KBr | " | 1.5 | .3 | 16.7 |
| (4) | 1% KBr + | 5.9 | 1.8 | 1.0 | 2.4 |
| (5) | 5% $K_2Cr_2O_7$ | " | 1.6 | 3.2 | 14.6 |
| (6) | 5% $K_2Cr_2O_7$ | " | 2.1 | 8.3 | 1.9 |

[1] t = 0: immediately before passing a 10 volt, 100 millisecond pulse.
t = 5 sec: 5 seconds after passing a 10 volt, 100 millisecond pulse.

In another experiment, 100 g-samples of aqueous solutions of KBr, and $K_2Cr_2O_7$ with KBr, were made. Ag-plated sensing elements were immersed in the solutions for about 30 hours and then checked coulometrically for the quantity of AgBr formed in a manner similar to the determination of AgCl explained earlier. The solutions and the electrical characteristics of the electrodes made using the Ag elements immersed for 50 hours with the respective solutions as electrolytes are shown below in Table VIII.

TABLE VIII

| | Solution | pH Initial | pH Final | Silver Halide (as millicoulomb equivalent) | No. Electrode pair | Polarization[1] t = 0 sec. (mv) | pulse 1 (mV) | pulse 2 (mV) |
|---|---|---|---|---|---|---|---|---|
| 1 | Distilled Water (as control) | 8.3 | 6.5 | 0, 0, | (1) | 26.3 | 219 | 271 |
| | | | | | (2) | 9.1 | 67 | 310 |
| 2 | 3% KBr | 9.3 | 7.2 | 7.5, 6 | (1) | .3 | 36.4 | 149 |
| | | | | | (2) | .7 | 23 | 33 |
| 3 | 3% KBr + 3% $K_2Cr_2O_7$ (pH adjusted by KOH to 4.7) | 4.7 | 4.95 | 21, 24, 24 | (1) | 1.5 | 22.5 | 48.1 |
| | | | | | (2) | 2.3 | 10.3 | 27.4 |
| 4 | 3% KBr + 3% $K_2Cr_2O_7$ (pH adjusted by KOH to 8) | 8 | 8.3 | 14, 9, 9 | (1) | .3 | 30.5 | 46.4 |
| | | | | | (2) | 3.1 | 36.4 | 51.1 |

[1] t = 0: Initial offset Potential, measured immediately before passing a 10 volt, 100 milliseconds pulse.
Pulse 1: Measured 5 seconds after passing a 10 volt, 100 millsecond pulse.
Pulse 2: Measured 5 seconds after passing a second 10 volt, 100 millisecond pulse.

It was concluded from the above data that Ag-AgBr electrodes are as effective as Ag-AgCl in providing non-polarizability to simulated defibrillation electrical pulses and that the oxidizing agent potassium dichromate increases the quantity of AgBr formed, especially at the lower pH of 4.7. This also resulted in expected lowering of the values of polarization over-voltage in the last column.

EXAMPLE 5

This example illustrates the use of non-aqueous solvents in the skin-interfacing material. With non-aqueous systems, there is little or no evaporation, thereby providing a longer shelf life. Furthermore, the possibility of chemical reactions occurring between metal parts of the electrode and water vapor from the gel is largely eliminated.

A 78 g sample of propylene glycol was heated to approximately 80° C. in a 150 ml glass beaker. Stirring was done by a magnetic stirrer. Eight-tenths g of KCl was added and stirring continued until the KCl dissolved. To this solution was added 0.12 gm. of $NaClO_2$. When dissolved, the stirring was stopped. The beaker was removed from the heat and cooled in tap water. The pH of the final mixture was 6. A 25 ml sample was placed in a glass bottle containing 10 silver-plated plastic sensing elements. The bottle was capped and stored at room temperature. Approximately 15 to 16 hours later some of the sensing elements were removed and tested for the amount of AgCl formed. Other elements were wiped clean and formed into "RED DOT" Brand No. 2256-type electrodes with a piece of polyurethane foam [(Scott Foam Co.) of 80 pore per inch] anchored to the sensing elements. The propylene glycol solution was impregnated into the foam. Four such electrodes were used on a human volunteer in the standard limb sites, and a high quality ECG trace was obtained. After removal, the electrodes were formed into pairs and tested for electrical characteristics. Results are shown in the following Table IX.

TABLE IX

| Electrode Pair No. | Impedance at 10 Hz Kohms | Polarization[1] | | | |
|---|---|---|---|---|---|
| | | t = 0 mV | Pulse 1 mV | Pulse 2 mV | Pulse 3 mV |
| (1) | 1.07 | 2.4 | 11.9 | 11 | 11 |
| (2) | 1.06 | 2.2 | 13.4 | 13.2 | 13 |

[1] t = 0: Initial offset voltage. Measured before passing Pulse 1.
Pulse 1: Voltage measured 5 seconds after passing a first 10V, 100 millisecond pulse.
Pulse 2: Voltage measured 5 seconds after passing a second 10V, 100 millisecond pulse.
Pulse 3: Voltage measured 5 seconds after passing a third 10V, 100 millisecond pulse.
The successive pulses were applied at approximately 20-second intervals.

The quantity of AgCl in millicoulomb equivalents on sensing elements from the same batch of electrodes was 54, 64 and 81.

The data show that the electrodes exhibit very good electrical characteristics as compared to standard aqueous gel electrodes. A sufficient amount of AgCl was formed in less than one day to pass repeated polarization pulses.

Another example of a non-aqueous system is illustrated by adding KCl and NaClO$_2$ in concentrations of 1.0 and 0.08 percent by weight, respectively to a conductive pressure sensitive material (described in U.S. Application Ser. No. 114,565 filed Sept. 4, 1979. The composition of the adhesive was as follows:

| Ingredient | Approx. % by Weight |
|---|---|
| Glycerin | 60 |
| Acrylic Acid | 25 |
| Polyacrylic Acid | 4 |
| Water | 5 |
| TEGBM (triethyleneglycol-bismethacrylate) | 0.3 |
| 2-Methoxy-2-phenyl acetate ("Irgacure" 651) | 0.01 |

To 26.6 g of the above adhesive precursor were added 3.4 g of an aqueous solution containing sodium chlorite (0.025 g) and potassium chloride (0.3 g). The mixture was placed under UV lamps for several minutes, followed by ten days under room ambient fluorescent light, during which time the mixture cured to an adhesive containing approximately 1% KCl and 0.08% sodium chlorite.

Two "RED DOT" Brand No. 2256 electrodes were made with sensing elements that had an overlying layer of the chlorite-containing adhesive. When tested after 5 days of aging for offset potential, impedance and polarization, the electrode pair gave results comparable to Ag/AgCl electrodes with conventional aqueous gels. Further, an ECG recording free from artifacts was also obtained.

Since the conductive adhesive is not a "water-based" electrolyte it does not dry out. Further, it has adhesive properties, thereby adhering the AgCl sensing element to the skin. This minimizes artifacts in the ECG recording caused by motion or stretching of the underlying skin.

EXAMPLE 6

This example illustrates the preparation of an electrode using a guar gum gel described in copending application Ser. No. 72,230, filed Sept. 4, 1979.

Solution A:

Distilled water (approximately 375 g) was heated to approximately 60° C. in a glass beaker. Potassium chloride (10.5 g) was added and stirred to dissolve.

Solution B:

In a separate beaker was placed propylene glycol (75 g), and to it, with mechanical stirring, were added successively guar gum (4 g, Stein-Hall HP-11), m-hydroxybenzoate (1 g) and p-hydroxybenzoate (0.2 g).

Solution B was added to Solution A, at approximately 60° C. with constant mechanical stirring, and mixing was continued until a homogenous solution was obtained. This was allowed to cool for about 15 hours, and then there was added a solution of sodium chlorite (0.25 g, in 1 ml water) with thorough mixing. This solution was called Solution C.

Potassium tetraborate (25 g of a 10% aqueous solution) was then added to Solution C, with vigorous mechanical stirring to help promote homogenous cross-linking of the gel which formed. The resulting gel had the following composition:

| Ingredient | % by Weight |
|---|---|
| Guar gum | 2 |
| Potassium chloride | 1 |
| Propylene glycol | 15 |
| Sodium chlorite | 0.05 |
| m-Hydroxybenzoate | 0.2 |
| p-Hydroxybenzoate | 0.04 |
| Potassium tetraborate (as 10% solution) | 5 |
| Water (to 100%) | approx. 77 |

The gel was placed by syringe into the gel cavity of "RED DOT" Brand No. 2256-style electrodes, fitted with silver sensing elements. After one week, the electrodes were tested, giving results as follows:

TABLE X

| Electrode Pair Number | Offset Potential (mV) | Impedance at 10 Hz (ohms) | Polarization[1] | | |
|---|---|---|---|---|---|
| | | | Pulse 1 mV | Pulse 2 mV | Pulse 3 mV |
| 1 | 0.8 | 500 | 16.6 | 20.5 | 21.3 |
| 2 | 0.7 | 470 | 17.1 | 19 | 21.4 |
| 3 | 1.2 | 510 | 17.7 | 20.1 | 20.2 |

[1] Voltages measured 5 seconds after each of three successive 100 volt, 25 millisecond pulses, applied at approximately 20 second intervals.

The silver chloride deposited on a random series of sensing elements selected for testing was, as coulomb equivalents, in millicoulombs: 63, 27, 45, 27, 36, 27, 63.

EXAMPLE 7

In another experiment, using a different guar gum gel composition and a different batch of sensing elements, but following the same procedure as Example 6, the following results were obtained.

| Gel Composition | |
|---|---|
| Ingredient | % by Weight |
| Guar gum | 2 |
| Potassium chloride | 2 |
| Propylene glycol | 20 |
| Sodium chlorite | 0.035 |
| Potassium tetraborate | 1.75 |
| Water (to 100%) | approx. 74 |

After aging four days, electrodes made with this gel had the following properties:

TABLE XI

| Electrode Pair Number | Offset Potential (mV) | Impedance at 10 Hz (ohms) | Polarization[1] Pulse 1 mV | Pulse 2 mV | Pulse 3 mV |
|---|---|---|---|---|---|
| 1 | 0.4 | 130 | 20.6 | 25 | 29.8 |
| 2 | 2.7 | 180 | 22.7 | 27 | 31 |
| 3 | 0.2 | 150 | 186 | 23 | 25.6 |

[1]Voltages measured 5 seconds after each of three successive 10 volt, 100 millisecond pulses, applied at approximately 20 second intervals.

EXAMPLE 8

This example illustrates the possible inhibitory effects of various ingredients in the skin-interfacing materials on the oxidizing agent. Experiments have shown that NaOCl ("HILEX" bleach) will oxidize silver to produce effective AgCl plating. However, the concentration of NaOCl required is higher than that of $NaClO_2$ for approximately the same rate of AgCl formation. "RED DOT" Brand No. 2256-type electrodes were made using a guar gum gel containing 1 percent KCl and different concentrations of "HILEX" bleach. The composition of the stock gel was as follows:

| Ingredient | % by Weight |
|---|---|
| Guar gum HP 11 (Stein Hall Co.*) | 2 |
| Propylene glycol | 10 |
| Potassium chloride | 1 |
| m-Hydroxybenzoate | 0.2 |
| p-Hydroxybenzoate | 0.04 |
| Water | 86.76 |

*Stein Hall Specialty Chemicals, New York, NY 10016

To make a 10% "HILEX"-containing gel, approximately 87.5 parts by weight of the stock solution were mixed well with 10 parts of "HILEX" bleach solution. Potassium tetraborate (approximately 2.5 parts of a saturated solution) was added with thorough stirring, to yield approximately 100 parts of a cross-linked, hypochlorite-containing guar gum gel.

The electrodes containing the guam gum gel were tested after various time periods. The results are shown in the following Table XII.

TABLE XII

| Pair No. | % of NaOCl bleach in gel | DC offset potential mV. | Impedance at 10 Hz ohms | Polarization[1] (mV) Pulse 1 | Pulse 2 |
|---|---|---|---|---|---|
| 1 | 10 | 0.6 | 280 | 112 | 146 |
| 2 | 10 | 0.4 | 285 | 89 | 109 |
| 3 | 35 | 0.2 | 44 | 11.2 | 2.3 |
| 4 | 35 | 0.3 | 47 | 2.1 | 3.6 |

[1]Measurements similar to those in Table VII.

Sensing elements placed in separate jars of gels for 15-20 hours were tested for the amount of AgCl formed. The following results were obtained.

TABLE XIII

| | Silver Chloride (in millicoulomb equivalents) |
|---|---|
| (1) 10% "HILEX" gel | 0, 0, 0 |
| (2) 35% "HILEX" gel | 390, 420, 390 |

Results confirm that a certain quantity of AgCl must be formed on the electrode's Ag sensing element before it will be non-polarizable.

In order to explain the absence of AgCl formation in the 10% gel, the following experiment was undertaken. One hundred gram solutions of "HILEX" bleach in distilled water were prepared. Solutions contained 10%, 20% and 35% by weight of bleach, respectively. To 20 g samples of each of the solutions were added 3.2 g of propylene glycol to obtain a 16% solution of glycol in the bleach. Further solutions included potassium tetraborate as well. To 20 g samples of these solutions, about 10 Ag-plated sensing elements were added and allowed to react for 30 minutes. After removal, they were rinsed in distilled water and air-dried at room conditions. The chlorided sensing elements were then stripped coulometrically to determine the quantity of AgCl formed.

The following results were obtained.

TABLE XIV

| | | Silver Chloride (in millicoulomb equivalents) | | |
|---|---|---|---|---|
| | | 10% | 20% | 35% |
| (1) | "HILEX" Bleach | pH = 7.55 63, 189, 207 | pH = 7.9 126, 216, 225 | pH = 8.1 99, 198, 225 |
| (2) | "HILEX" Bleach + 16% water | pH = 7.55 225, 240, 261 | pH = 8 240, 255, 255 | pH = 8.15 285, 285, 300 |
| (3) | "HILEX" Bleach + 16% propylene glycol | pH = 8.1 126, 144, 162 | pH = 8.1 72, 99, 144 | pH = 8.1 45, 126, 126 |
| (4) | "HILEX" Bleach + 16% propylene glycol + 1.6% of a 20% solution of $K_2B_4O_7 \cdot 4H_2O$ (potassium tetraborate) | pH = 7.5 54, 63, 96 | pH = 7.5 54, 72, 81 | pH = 7.5 45, 54, 63 |

The data in Table XIV clearly indicate the inhibitory action of propylene glycol and the potassium tetraborate on the formation of AgCl by the NaOCl solution. Since propylene glycol and borate are essential components of the guar gum gel, the lack of AgCl formation in the experiments is explained. The use of sodium chlorite on the other hand, does not seem to indicate this phenomenon of interactive inhibition of Ag oxidation, as indicated in previous examples.

EXAMPLE 9

LECTRON III gel was purchased already containing KCl, 2% by weight. To this gel (3 kgs) was added a solution of 1.5 gms (0.05%) of reagent grade sodium chlorite (Matheson, Coleman and Bell, 2909 Highland Avenue, Cincinnati Ohio 45212) in about 10 ml of distilled water, with thorough mechanical mixing.

Electrodes, otherwise similar to 3M Red Dot No. 2246 electrodes (3M Company, 3M Center, St. Paul, Minn. 55144) but having a silver-plated sensing element, were made using the chlorite gel prepared above. They were stored at room temperature for one month. Thereafter the samples were divided into three lots of samples which were stored respectively at ambient unheated storage conditions (subzero to over 90° F.); room temperature; and 100° F. for six months. Samples were tested from time to time and the one month and six month data are presented in Table XV.

EXAMPLE 10

LECTRON III gel, containing 2% KCl, was combined with sodium chlorite (0.025%) after the method of Example 9. Similar electrodes were filled with this gel, following the same procedure. Samples of these electrodes were stored, aged and tested in the same way as in Example 9, and the test results are likewise given in Table XV.

EXAMPLE 11

As a control, electrodes of the current art, made with the same sensing elements as those used in Examples 9 and 10 but separately chlorided prior to assembly, and using a similar gel without any sodium chlorite, were similarly stored, aged and tested. The results are given in Table XV.

TABLE XV

| Example | Percent NaClO₂ in gel | Storage Period | OFFSET POTENTIAL in mV per pair (mean/S.D.) | | | A.C. IMPEDANCE at 10Hz in Ohms per pair (mean/S.D.) | | | POLARIZATION[1] in mV per pair mean/S.D. | | | Silver Chloride Coulomb equivalents in millicoulombs per sensing element Mean/S.D. | | |
|---|---|---|---|---|---|---|---|---|---|---|---|---|---|---|
| | | | Ambient | Room Temp | 100° F | Ambient | Room Temp | 100° F | Ambient | Room Temp | 100° F | Ambient | Room Temp | 100° F |
| 9 | 0.05 | 1 month | .23/.11 | .66/.56 | .52/.41 | 405/34 | 481/29 | 498/47 | 14/.9 | 13.2/.8 | 13/.8 | 308/32 | 206/31 | 328/84 |
| | | 6 months | 1.4/1.5 | 1.6/.9 | 1.6/1.1 | 407/37 | 536/46 | 538/94 | 13.1/1.4 | 14.8/1.1 | 14/.4 | 317/25 | 450/71 | 426/49 |
| 10 | 0.025 | 1 month | .4/.3 | .5/15 | .76/.56 | 460/27 | 463/27 | 466/33 | 13.7/2.2 | 15.1/2.3 | 15.3/2.7 | 95/5 | 92/7 | 92/11 |
| | | 6 months | 1.5/1.4 | 1.4/.9 | 2.4/1.3 | 460/33 | 448/35 | 461/47 | 11.8/1.3 | 12/.8 | 13/3 | 113/8 | 122/21 | 104/42 |
| 11 | 0 | 1 month | .7/.57 | 2.6/2.2 | 1.3/.9 | 101/4 | 107/5.1 | 118/39 | 16.8/1.2 | 22.7/12 | 18.8/1.3 | 258/33 | 241/121 | 252/51 |
| | | 6 months | .9/.4 | 1.6/1.2 | 2.7/2.1 | 110/20 | 112/12 | 172/63 | 15.2/.7 | 17.1/1.4 | 16.1/.6 | 263/43 | 249/41 | 269/33 |

[1]Voltages measured 5 seconds after the third of three 10 V, 100 millisecond pulses applied successively at approximately 20 second intervals.
(Each data point is averaged from a minimum of twelve pairs of electrodes.)

What is claimed is:

1. A non-polarizable biomedical electrode comprising:
   an electrical impulse-sensing element having a metallic surface, said sensing element having a base portion with a lower skin-directed surface and an upper surface having means for connection to an electromedical testing apparatus; and
   a conformable, electrically-conductive skin-interfacing material in electrical contact with said lower surface of said sensing element comprising a solvent having dissolved therein an oxidizing agent capable of oxidizing the metal on said lower surface of said sensing element to form a metallic cation, and an electrolyte salt in sufficient quantity to render said skin-interfacing material electrically-conductive, the anion of said salt being capable of reacting with said metallic cation to form an insoluble compound on said lower surface of said sensing element which causes the electrode to be non-polarizable.

2. The electrode according to claim 1 wherein the metallic surface of said sensing element is silver.

3. The electrode according to claim 2 wherein said insoluble compound is a silver halide.

4. The electrode according to claim 3 wherein said silver halide is silver chloride.

5. The electrode according to claim 2 wherein said anion of said electrolyte salt is Cl⁻.

6. The electrode according to claim 5 wherein said anion is present in an amount between about 0.1 and 10 percent by weight of said skin-interfacing material.

7. The electrode according to claim 5 wherein said electrolyte salt is selected from the group consisting of NaCl and KCl.

8. The electrode according to claim 2 wherein said oxidizing agent is selected from the group consisting of $NaClO_2$, NaOCl and $NaClO_3$.

9. The electrode according to claim 8 wherin said oxidizing agent is $NaClO_2$.

10. The electrode according to claim 9 wherein said oxidizing agent is present in an amount between about 0.001 and 0.75 percent by weight of said skin-interfacing material.

11. The electrode according to claim 1 wherein said solvent is water containing a conventional thickening agent.

12. A conformable electrically-conductive composition for use as the interfacing material between the skin and the metallic sensing element of a biomedical electrode comprising a solvent having dissolved therein an oxidizing agent capable of providing chlorite ions in solution to oxidize the metal on the surface of said sensing element to form a metallic cation, and an electrolyte salt in sufficient quantity to render said composition electrically-conductive, the anion of said salt being capable of reacting with said metallic cation to form an insoluble compound on the surface of said sensing element, said chlorite ion- providing oxidizing agent being present in an amount sufficient to form enough of said insoluble compound on the surface of said sensing element to cause the electrode to be non-polarizable.

13. The composition according to claim 12 wherein said metallic sensing element is silver.

14. The composition according to claim 13 wherein said insoluble compound is a silver halide.

15. The composition according to claim 14 wherein said silver halide is silver chloride.

16. The composition according to claim 12 wherein said electrolyte salt is selected from the group consisting of NaCl and KCl.

17. The composition according to claim 12 wherein said oxidizing agent is $NaClO_2$.

* * * * *